US008153160B2

(12) United States Patent
Ohm et al.

(10) Patent No.: US 8,153,160 B2
(45) Date of Patent: Apr. 10, 2012

(54) PHARMACEUTICAL DOSAGE FORMS COMPRISING AN ACTIVE INGREDIENT COMBINATION OF NIFEDIPINE AND/OR NISOLDIPINE AND AN ANGIOTENSIN II ANTAGONIST

(75) Inventors: Andreas Ohm, Neuss (DE); Klaus Benke, Bergisch Gladbach (DE); Hanna Tinel, Wuppertal (DE); Joachim Hütter, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 560 days.

(21) Appl. No.: 11/922,745

(22) PCT Filed: Jun. 29, 2006

(86) PCT No.: PCT/EP2006/006293
§ 371 (c)(1),
(2), (4) Date: Mar. 13, 2009

(87) PCT Pub. No.: WO2007/003330
PCT Pub. Date: Jan. 11, 2007

(65) Prior Publication Data
US 2009/0214664 A1 Aug. 27, 2009

(30) Foreign Application Priority Data
Jul. 6, 2005 (DE) .......................... 10 2005 031 577

(51) Int. Cl.
*A61K 9/16* (2006.01)
(52) U.S. Cl. ...................................................... 424/497
(58) Field of Classification Search .................. None
See application file for complete search history.

(56) References Cited

U.S. PATENT DOCUMENTS

| 4,327,725 A | 5/1982 | Cortese et al. |
| 4,612,008 A | 9/1986 | Wong et al. |
| 4,765,989 A | 8/1988 | Wong et al. |
| 4,783,337 A | 11/1988 | Wong et al. |
| 4,892,741 A | 1/1990 | Ohm et al. |
| 4,948,592 A | 8/1990 | Ayer et al. |
| 5,082,668 A | 1/1992 | Wong et al. |
| 5,204,121 A | 4/1993 | Bucheler et al. |
| 5,543,154 A | 8/1996 | Rork et al. |
| 6,294,201 B1 | 9/2001 | Kettelhoit et al. |
| 6,555,136 B2 | 4/2003 | Midha |
| 2003/0161882 A1 | 8/2003 | Waterman |
| 2004/0115134 A1* | 6/2004 | Merisko-Liversidge ....... 424/45 |
| 2005/0008702 A1 | 1/2005 | Faour et al. |
| 2009/0214664 A1 | 8/2009 | Ohm et al. |

FOREIGN PATENT DOCUMENTS

| AU | 2003227472 A1 | 3/2003 |
| DE | 19747261 | 4/1999 |
| EP | 0339811 A2 | 4/1989 |
| EP | 0776660 A2 | 4/1997 |
| EP | 1413315 | 4/2004 |
| GB | 2140687 | 12/1984 |
| IE | 56515 B1 | 5/1983 |
| WO | WO 92/10097 | 6/1992 |
| WO | 9300071 A1 | 1/1993 |
| WO | 9303711 A1 | 9/1993 |
| WO | WO 03/035039 | 5/2003 |
| WO | 03097045 A1 | 11/2003 |
| WO | WO 2005/009412 | 2/2005 |
| WO | 2008044862 A1 | 4/2008 |

OTHER PUBLICATIONS

K. Hayashi, et al.: "Disparate Effects of Calcium Antagonists on Renal Microcirculation," Hypertens Res., No. 19, 1996, pp. 31-36.
K. Kubo, et al.: "Nonpeptide Angiostensin II Receptor Antagonists. Synthesis and Biological Activity of Potential Prodrugs of Benzimidazole-7-Carboxylic Acids," Journal Medical Chemistry, No. 36, 1993, pp. 2343-2349.
B. C. Lippold: "Controlled Release Products: Approaches of Pharmaceutical Technology," Düsseldorf, Wiss. Verl. -Ges., 1989, pp. 39-57.
G. Santus, et al.: "Osmotic Drug Delivery: a Review of the Patent Literature," Journal of Controlled Release, No. 35, 1995, pp. 1-21.
R. K. Verma et al.: "Formulation Aspects in the Development of Osmotically Controlled Oral Drug Delivery Systems," Journal of Controlled Release, No. 79, 2002, pp. 7-27.
R. K. Verma et al.: "Osmotic Pumps in Drug Delivery," Critical Reviews in Therapeutic Drug Carrier Systems, vol. 21, No. 6, 2004, pp. 477-520.
R. K. Verma et al.: "Osmotically Controlled Oral Drug Delivery," Drug Development and Industrial Pharmacy, vol. 26, No. 7, 2002, pp. 695-708.
European Patent Office English translation of claims of DE 19747261.
Hasebe et al., "Controlled-release nifedipine and candesartan low-dose combination therapy in patients with essential hypertension: the NICE Combi (Nifedipine and Candesartan Combination) Study", Journal of Hypertension, 2005, vol. 23, No. 2, pp. 445-453, Lippincott Williams & Wilkins, 2005.
Jamerson, et al., "Benazepril plus Amlodipine or Hydroxyhlorothiazide for Hypertension in High-Risk Patients," N. Engl. J. Med. 2008, vol. 359, No. 23, 2417-2428.

* cited by examiner

*Primary Examiner* — Bethany Barham
(74) *Attorney, Agent, or Firm* — Karen B. King

(57) ABSTRACT

The present invention relates to a pharmaceutical dosage form comprising an active ingredient combination of nifedipine and/or nisoldipine and at least one angiotensin II antagonist, characterized in that the active ingredient combination undergoes controlled (modified) release in the body, and to processes for the production thereof, to the use thereof as pharmaceuticals, to the use thereof for the prophylaxis, secondary prophylaxis and/or treatment of disorders, and to the use thereof for manufacturing a pharmaceutical for the prophylaxis, secondary prophylaxis and/or treatment of disorders.

38 Claims, No Drawings

PHARMACEUTICAL DOSAGE FORMS COMPRISING AN ACTIVE INGREDIENT COMBINATION OF NIFEDIPINE AND/OR NISOLDIPINE AND AN ANGIOTENSIN II ANTAGONIST

The present invention relates to a pharmaceutical dosage form comprising an active ingredient combination of nifedipine and/or nisoldipine and at least one angiotensin II antagonist, characterized in that the active ingredient combination undergoes controlled (modified) release in the body, and to processes for the production thereof, to the use thereof as pharmaceuticals, to the use thereof for the prophylaxis, secondary prophylaxis and/or treatment of disorders, and to the use thereof for manufacturing a pharmaceutical for the prophylaxis, secondary prophylaxis and/or treatment of disorders.

Calcium antagonists such as, for example, nifedipine and nisoldipine are successfully employed as established drugs in the therapy of high blood pressure. The examples mentioned are well known to the skilled worker and are described in the relevant literature. Through their direct effect on the arterial blood vessels, they reduce the blood pressure reliably in a large proportion of patients. However, they bring about an increase in the filtration pressure in the kidney through preferential dilatation of the afferent arterioles. Where the kidney has previously been damaged, this may lead to an increased stress on the filtration apparatus and be manifested by proteinuria in patients. This effect can be prevented by addition of a therapeutically effective dose of an angiotensin II antagonist. Suitable angiotensin II antagonists are all known angiotensin II antagonists and preferably and for example candesartan, irbesartan, losartan, telmisartan and olmesartan. The examples mentioned are well known to the skilled worker and are described in the relevant literature. Since angiotensin II antagonists also have a dilating effect in the region of the efferent arteriole, additional administration of these substances can prevent the unwanted increase in the filtration pressure.

As disclosed in Hayashi K; Nagahama T, Oka K, Epstein M, Sarute T: Disparate effects of calcium antagonists on renal microcirculation. *Hypertens Res* 1996:19:31-36, combination of nifedipine and/or nisoldipine with an angiotensin II antagonist therefore brings about a very good reduction in blood pressure together with lower stress on the kidney. This represents a considerable therapeutic advance. It is additionally possible by the combination of such to reduce other side effects such as the peripheral edemas which occur with calcium antagonists, and the stimulation, caused by reflex release of norepinephrine, of the sympathetic nervous system.

In cases of diseases which require treatment over a lengthy period, or for the long-term prophylaxis of diseases, it is desirable to keep the frequency of intake of medicaments as low as possible. This is not only more convenient for the patient, it also increases the reliability of treatment by reducing the disadvantages of irregular intake. The desired reduction in the frequency of intake, for example from administration twice a day to once a day, can be achieved by prolonging the therapeutically effective plasma levels by modified release of active ingredients from the dosage forms.

After intake of dosage forms with modified active ingredient release it is additionally possible to reduced, by smoothing the course of the plasma levels (minimizing the so-called peak-trough ratio), i.e. by avoiding high plasma active ingredient concentrations which are to be observed frequently after administration of fast-release pharmaceutical forms, the occurrence of unwanted side effects which correlate with the concentration peaks.

It is advantageous especially for the long-term therapy or prophylaxis and secondary prophylaxis of cardiovascular disorders to have the active ingredients available in a form which, through a modified release of active ingredients, leads to a reduction in the peak-trough ratio and makes administration once a day possible.

In the development of formulations, account must also be taken of the physicochemical and biological properties of the active ingredients, for example the relatively low water solubility of nifedipine (approx. 9 mg/l) and the plasma half-life of about 2 hours. Accordingly, special pharmaceutical formulations with which nifedipine and/or nisoldipine undergoes a modified release, taking account of its physicochemical and biological properties, are necessary for the desired administration once a day.

The angiotensin II antagonists in the form of their commercial products are all marketed as fast-release (immediate-release) formulations because, despite their short dominant plasma half-life, their effect persists for more than 24 hours. Nevertheless, a slowing of active ingredient delivery, i.e. controlled release of the angiotensin II antagonist over many hours, is advantageous in relation to avoiding large peak-trough fluctuations. It is thus possible to avoid extreme plasma level peaks, which are not required for the effect, and, at the same time, to increase and ensure the 24-hour plasma levels with comparatively the same or even a lower dose than the marketed commercial product. The slowing of release thus makes the supply of active ingredient to the patient optimal for the desired effect (uniform plasma level/time profile).

In view of the biological properties of nifedipine and/or nisoldipine and the angiotensin II antagonists, it is crucial for both active ingredients to be absorbed from the low sections of the bowel without significant loss of bioavailability. This is the case with only about 30-50% of all active ingredients, and therefore appropriate selection of the combination active ingredients is crucially important for developing a slow-release combination product.

Various methods are known for producing pharmaceutical dosage forms with modified release; see, for example, B. Lippold in "Oral Controlled Release Products: Therapeutic and Biopharmaceutic Assessment" Editors U. Gundert-Remy and H. Möller, Stuttgart, Wiss.Verl.-Ges., 1989, 39-57.

These systems are not generally suitable for slowing the release of an active ingredient combination, especially also in the case of active ingredients with very different phys.-chem. properties, especially when the active ingredient delivery rate of the combination partners is not to differ significantly from one another. It is therefore necessary, besides the different dosages, to take account in particular of the solubility of the active ingredients. Thus, the water solubility of the angiotensin II antagonist Losartan-K is classified as "freely soluble", whereas candesartan cilexetil is classified as virtually insoluble in water. The water solubility of the combination partner nifedipine is 9 mg/l and that of nisoldipine is about 2 mg/l.

It has now been found, surprisingly, that the dosage forms of the invention, which release the active ingredients with a particular, defined modified rate, make administration once a day possible with comparatively constant plasma concentrations. The slow-release pharmaceutical forms of the invention now release the two active ingredients with a comparable delivery rate.

Particularly suitable dosage forms with modified/slow release of the active ingredients are based on osmotic release systems. In these, cores, for example capsules or tablets, preferably tablets, are surrounded by a semipermeable membrane which has at least one orifice. The water-permeable membrane is impermeable for components of the core, but allows water to enter the system from outside by osmosis. The water which has penetrated in then releases, by the resulting osmotic pressure, the active ingredient in dissolved or suspended form from the orifice(s) in the membrane. The overall active ingredient release and the release rate can be controlled substantially via the thickness and porosity of the semipermeable membrane, the composition of the core and the number and size of the orifice(s). Advantages, formulation aspects, use forms and information on production processes are described inter alia in the following publications:

Santus, G., Baker, R. W., "Osmotic drug delivery: a review of the patent literature", Journal of Controlled Release 35 (1995), 1-21

Verma, R. K., Mishra, B., Garg, S., "Osmotically controlled oral drug delivery", Drug Development and Industrial Pharmacy 26 (7), 695-708 (2000)

Verma, R. K., Krishna, D. M., Garg, S., "Formulation aspects in the development of osmotically controlled oral drug delivery systems", Journal of Controlled Release 79 (2002), 7-27

Verma, R. K., Arora, S., Garg, S., "Osmotic pumps in drug delivery", Critical Reviews in Therapeutic Drug Carrier Systems 21 (6) (2004), 477-520

U.S. Pat. No. 4,327,725, U.S. Pat. No. 4,765,989, US 20030161882, EP 1 024 793.

The present invention relates to pharmaceutical dosage form comprising an active ingredient combination of nifedipine or nisoldipine and at least one angiotensin II antagonist, characterized in that the active ingredient combination undergoes controlled (modified) release in the body.

The invention further relates preferably to a pharmaceutical dosage form comprising an active ingredient combination of nifedipine or nisoldipine and at least one angiotensin II antagonist, characterized in that the active ingredient combination undergoes controlled (modified) release in the body on the basis of an osmotic active ingredient release system.

The angiotensin II antagonists preferably used are candesartan, losartan, telmisartan, irbesartan and olmesarten or prodrugs thereof. The term "prodrugs" includes compounds which may themselves be biologically active or inactive but are converted (for example by metabolism or hydrolysis) during their residence time in the body into the compounds used according to the invention. A prodrug of candesartan is for example candesartan cilexetil. This and further examples of suitable prodrugs are disclosed in J. Med. Chem. 1993 Aug. 6; 36(16):2343-9. A prodrug of olmesartan is for example Olmesartan medoxomil.

The dosage form of the invention preferably comprises nifedipine or nisoldipine in dosages of from 5 to 60 mg, preferably in dosages of from 10 to 40 mg and at least one angiotensin II antagonist in dosages of from 2 to 500 mg, preferably candesartan in dosages of from 2 to 32 mg, preferably from 4 to 16 mg, likewise preferably olmesartan in a dosage of from 5 to 40 mg, preferably from 10 to 40 mg, likewise preferably telmisartan in a dosage of from 10 to 80 mg, preferably from 10 to 40 mg, likewise preferably losartan in a dosage of from 25 to 100 mg, preferably from 40 to 60 mg, likewise preferably irbesartan in a dosage of from 50 to 500 mg, preferably from 75 to 300 mg.

It may be necessary where appropriate to deviate from the stated amounts, in particular as a function of the body weight or of the type of administration route, the individual behavior toward the medicaments, the type of formulation thereof and the time or interval over which administration takes place. Thus, it may in some cases be sufficient to make do with less than the aforementioned minimum amount, whereas in other cases the stated upper limit must be exceeded.

The invention further relates to solid pharmaceutical dosage forms for administration once a day which can be administered orally, comprise an active ingredient combination of nifedipine or nisoldipine with an angiotensin II antagonist and are based on osmotic delivery systems, characterized in that 80% of the active ingredients (based on the declared total amount of the respective active ingredient) are released over a period of at least 4 and at most 30 hours in the USP release method with apparatus 2 (paddle). In this connection, the delivery rate of the angiotensin II antagonist combined with nifedipine or nisoldipine does not differ significantly from the delivery rate in the linear phase of release of nifedipine or nisoldipine, preferably by not more than 25% relative to nifedipine and/or nisoldipine, particularly preferably by less than 15%.

In a preferred embodiment of the present invention, 80% of the active ingredients are released in a period of from 8 to 24 hours in the USP release method with apparatus 2 (paddle).

The active ingredients may be present in the pharmaceutical dosage forms of the invention in crystalline form or in noncrystalline amorphous form, or in mixtures of crystalline and amorphous active ingredient portions.

If the dosage forms of the invention comprise the active ingredients in crystalline form, they are employed in micronized form in a preferred embodiment of the present invention. In this connection, nifedipine or nisoldipine preferably have an average particle size $X_{50}$ of 2-6 μm and an $X_{90}$ value (90% portion) of less than 12 μm.

Both osmotic single-chamber systems (elementary osmotic pump) and two-chamber systems (push-pull systems) are suitable for the active ingredient combination.

The shell of the osmotic pharmaceutical release system consists, in both the single-chamber system and in the two-chamber system, of a water-permeable material which is impermeable for the components of the core. Such shell materials are known in principle and described for example in EP-B1-1 024 793, pages 3-4, the disclosure of which is incorporated herein by reference. Preferably employed as shell material according to the invention are cellulose acetate or mixtures of cellulose acetate and polyethylene glycol.

A coating, for example a photoprotective and/or colored coating, can be applied to the shell if required. Materials suitable for this purpose are for example polymers such as polyvinyl alcohol, hydroxypropylcellulose and/or hydroxypropylmethylcellulose, where appropriate in combination with suitable plasticizers such as, for example, polyethylene glycol or polypropylene glycol and pigments such as, for example, titanium dioxide or iron oxides.

The core in the osmotic single-chamber system preferably comprises:

5 to 50% of the active ingredient combination of nifedipine or nisoldipine+angiotensin II antagonists, 10 to 50% xanthan, 5 to 40% of a vinylpyrrolidone-vinyl acetate copolymer, where the difference from 100% is formed where appropriate by one or more additional ingredients selected from the group of further hydrophilic, swellable polymers, osmotically active additives and pharmaceutically usual excipients. The total of the core ingredients amounts to 100%, and the % data are based in each case on the total mass of the core.

The osmotic single-chamber system comprises as one of the essential ingredients of the core the hydrophilic water-swellable polymer xanthan. This is an anionic heteropolysaccharide which is obtainable commercially for example under the name Rhodigel® (produced by Rhodia). It is present in an amount of from 10 to 50%, preferably from 20 to 40%, based on the total mass of the core ingredients.

A further essential ingredient of the core is the vinylpyrrolidone-vinyl acetate copolymer. This copolymer is known per se and can be produced with any desired monomer mixing ratios. The commercially available Kollidon® VA64 (produced by BASF) which is preferably used is, for example, a 60:40 copolymer. It generally has a weight average molecular weight Mw, determined by light-scattering measurements, of about 45 000 to about 70 000. The amount of the vinylpyrrolidone-vinyl acetate copolymer in the core is 5 to 40%, preferably 15 to 25%, based on the total mass of the core ingredients.

Hydrophilic swellable polymers which are additionally present where appropriate in the core are, for example, hydroxypropylcellulose, hydroxypropylmethylcellulose, sodium carboxymethyl-cellulose, sodium carboxymethyl starch, polyacrylic acids and salts thereof.

Osmotically active additives which are additionally present where appropriate in the core are, for example, all water-soluble substances acceptable for use in pharmacy, such as, for example, the water-soluble excipients mentioned in pharmacopeias or in "Hager" and "Remington Pharmaceutical Science". It is possible in particular to use water-soluble salts of inorganic or organic acids or nonionic organic substances with high solubility in water, such as, for example, carbohydrates, especially sugars, sugar alcohols or amino acids. For example, the osmotically active additives can be selected from inorganic salts such as chlorides, sulfates, carbonates and bicarbonates of alkali metals or alkaline earth metals, such as lithium, sodium, potassium, magnesium, calcium, and phosphates, hydrogen phosphates or dihydrogen phosphates, acetates, succinates, benzoates, citrates or ascorbates thereof. It is furthermore possible to use pentoses such as arabinose, ribose or xylose, hexoses such as glucose, fructose, galactose or mannose, disaccharides such as sucrose, maltose or lactose or trisaccharides such as raffinose. The water-soluble amino acids include glycine, leucine, alanine or methionine. Sodium chloride is particularly preferably used according to the invention. The osmotically active additives are preferably present in an amount of up to 30% based on the total mass of the core ingredients.

Pharmaceutically usual excipients which are additionally present where appropriate in the core are, for example, buffer substances such as sodium bicarbonate, binders such as hydroxypropylcellulose, hydroxypropylmethylcellulose and/or polyvinylpyrrolidone, lubricants such as magnesium stearate, wetting agents such as sodium lauryl sulfate and/or flow regulators such as colloidal silicon dioxide and stabilizers such as antioxidants.

The present invention further relates to a process for producing an osmotic single-chamber system of the invention, where the components of the core are mixed together, subjected where appropriate to wet or dry granulation, and subsequently tabletted, and the core produced in this way is coated with the shell which is then covered where appropriate with a photoprotective and/or colored coating, and which is provided with one or more orifices.

In a preferred embodiment of the present invention, the core components are subjected to a wet granulation during the production of the osmotic single-chamber system, because this process step improves the wettability of the ingredients of the tablet core, resulting in better penetration of the core by the entering gastrointestinal fluid, which frequently leads to faster and more complete release of the active ingredient.

In the osmotic two-chamber system, the core consists of two layers, one active ingredient layer and one osmosis layer. An osmotic two-chamber system of this type is described in detail for example in DE 34 17 113 C 2, the disclosure of which is incorporated herein by reference.

The active ingredient layer preferably comprises:
  5 to 50% of the active ingredient combination of nifedipine or nisoldipine+angiotensin II antagonist,
  40 to 95% of one or more osmotically active polymers, preferably polyethylene oxide of medium viscosity (40 to 100 mPa·s; 5% strength aqueous solution, 25° C.).

The osmosis layer preferably comprises:
  40 to 90% of one or more osmotically active polymers, preferably polyethylene oxide of high viscosity (5000 to 8000 mPa·s; 1% strength aqueous solution, 25° C.).
  5 to 40% of an osmotically active additive,
where the difference from 100% in the individual layers is formed in each case independently of one another by one or more additional ingredients in the form of pharmaceutically usual excipients. The % data are in each case based on the total mass of the particular core layer.

The osmotically active additives used in the core of the osmotic two-chamber system may furthermore be the same as in the case of the single-chamber system described above. Sodium chloride is preferred in this connection.

The pharmaceutically usual excipients used in the core of the osmotic two-chamber system may be the same as in the case of the single-chamber system described above. Preference is given in this connection to binders such as hydroxypropylcellulose, hydroxypropylmethylcellulose and/or polyvinylpyrrolidone, lubricants such as magnesium stearate, wetting agents such as sodium lauryl sulfate and/or flow regulators such as colloidal silicon dioxide, and a coloring pigment such as iron oxide in one of the two layers to differentiate active ingredient layer and osmosis layer, and stabilizers/antioxidants in the active ingredient layer.

The present invention further relates to a process for producing the osmotic two-chamber system according to the invention, where the components of the active ingredient layer are mixed and granulated, the components of the osmosis layer are mixed and granulated, and then the two granules are compressed to a bilayer tablet in a bilayer tablet press. The core produced in this way is then coated with a shell, and the shell is provided with one or more orifices on the active ingredient side and subsequently also covered where appropriate with a coating.

In a preferred embodiment of the present invention, both the components of the active ingredient layer and the components of the osmosis layer are each subjected to granulation, in particular by means of roller granulation, in the production of the osmotic two-chamber system.

Preference is given according to the invention, because of the physicochemical properties of the active ingredient combination, to osmotic two-chamber systems (push-pull systems) in which the active ingredient layer and osmosis layer are separated, by way of example and advantageously formulated as 2-layer tablet. The advantages over osmotic single-chamber systems are in this case that the release rate is more uniform over a longer period, and that it is possible to reduce the system-related need for an excess of active ingredient.

The present invention further relates to oral pharmaceuticals which can be administered once a day and comprise a solid pharmaceutical dosage form of the invention which comprises the active ingredient combination of nifedipine or nisoldipine and at least one angiotensin II antagonist and has modified release.

The present invention further relates preferably to oral pharmaceuticals which can be administered once a day and comprise a solid pharmaceutical dosage form of the invention which comprises the active ingredient combination of nifedipine or nisoldipine and at least one angiotensin II antagonist and has modified release achieved by osmotic active ingredient release systems.

The present invention further relates to the use of the solid pharmaceutical dosage forms which can be administered orally, comprise an active ingredient combination of nifedipine or nisoldipine with at least one angiotensin II antagonist, and are based on osmotic delivery systems for the prophylaxis, secondary prophylaxis and/or treatment of cardiovascular disorders, e.g. high blood pressure.

The present invention further relates to the use of the solid pharmaceutical dosage forms which can be administered orally, comprise an active ingredient combination of nifedipine or nisoldipine with at least one angiotensin II antagonist, and are based on osmotic delivery systems for the manufacture of a pharmaceutical for the prophylaxis, secondary prophylaxis and/or treatment of cardiovascular disorders, e.g. high blood pressure.

The present invention further relates to the use of an active ingredient combination of nifedipine or nisoldipine with at least one angiotensin II antagonist for the manufacture of a solid pharmaceutical for the dosage form of the invention which can be administered orally and is based on osmotic delivery systems.

The present invention further relates to a method for the prophylaxis, secondary prophylaxis and/or treatment of cardiovascular disorders by administering a solid pharmaceutical dosage form of the invention which can be administered orally and comprises the active ingredient combination of nifedipine or nisoldipine and at least one angiotensin II antagonist and has an osmotic release system.

The present invention further relates to a triple combination of antihypertensive medicaments comprising nifedipine or nisoldipine, at least one angiotensin II antagonist and at least one further antihypertensive agent. Preference is given to a diuretic and particular preference to hydrochlorothiazide.

This combination is particularly suitable for the treatment of patients in whom monotherapy or the dual combination therapy has not brought about the desired reduction in blood pressure. The therapy-resistant patients are often among the patients for whom appropriate control of blood pressure is particularly important. Although calcium antagonists and diuretics are both medicaments which reduce the blood pressure independently of the renin-angiontensin system, they differ in the mechanism of action. Calcium antagonists are primarily vasodilators with a weak natriuretic effect, whereas the opposite applies to diuretics (thiazides). If the renin-angiotensin system is inhibited, the diuretics and calcium antagonists have an additive affect. It has surprisingly been possible to show that the triple combination described above led to an appropriate control of blood pressure even in therapy-resistant patients.

The invention is explained in more detail below by preferred exemplary embodiments, but is not restricted thereto. Unless indicated otherwise, all quantitative data below are based on percentages by weight.

Experimental Section

The in vitro release investigations described below were carried out by the USP release method with apparatus 2 (paddle). The speed of rotation of the stirrer is 100 rpm (revolutions per minute) in 900 ml of a phosphate buffer solution of pH 6.8, which was prepared from 1.25 ml of ortho-phosphoric acid, 4.75 g of citric acid monohydrate and 27.46 g of disodium hydrogen phosphate dihydrate in 10 l of water. Also added to the buffer solution to set up sink conditions is 1% sodium lauryl sulfate. The tablet formulations are preferably released from a sinker as specified in the Japanese Pharmacopoeia.

1. Osmotic Single-Chamber System Comprising Nifedipine/Angiotensin II Antagonist Combination

| Exemplary formulation 1.1 Tablet composition in mg/tablet (declared content = 20 mg of nifedipine plus 8 mg of candesartan/tablet) | |
|---|---|
| Core | |
| Nifedipine, micronized | 24.0 mg |
| Candesartan cilexetil | 9.6 mg |
| Xanthan gum (Rhodigel TSC, Rhodia) | 100.0 mg |
| Copolyvidone (Kollidon VA 64, BASF) | 56.0 mg |
| Sodium chloride | 56.0 mg |
| Sodium bicarbonate | 17.9 mg |
| Sodium carboxymethyl starch | 23.0 mg |
| Hydroxypropylmethylcellulose (5 cp) | 10.0 mg |
| Sodium lauryl sulfate | 0.5 mg |
| Colloidal silicon dioxide (Aerosil 200, Degussa) | 1.5 mg |
| Magnesium stearate | 1.5 mg |
| | 300.0 mg |
| Shell (osmotic membrane) | |
| Cellulose acetate | 22.8 mg |
| Polyethylene glycol 3.350 | 1.2 mg |
| | 24.0 mg |

Production:

Xanthan gum, copolyvidone, sodium chloride, sodium bicarbonate and sodium carboxymethyl-cellulose are mixed and then undergo wet granulation with an aqueous suspension of the active ingredients nifedipine and candesartan cilexetil and hydroxypropylmethylcellulose. Drying and screening are followed by admixture of Aerosil and magnesium stearate, and the resulting mixture ready for compression is compressed to tablets with a diameter of 8 mm. The tablet cores are coated with an acetone solution of cellulose acetate and polyethylene glycol and dried. Two orifices each with a diameter of 1 mm are then made in each tablet using a hand drill.

2. Osmotic Two-Chamber System Comprising Nifedipine/Angiotensin II Antagonist Combination

| Exemplary formulation 2.1 Tablet composition in mg/tablet (declared content = 30 mg of nifedipine plus 50 mg of losartan potassium/tablet) | |
|---|---|
| Core Active ingredient layer | |
| Nifedipine, micronized | 33.0 mg |
| Losartan-K granules * | 155.0 mg |
| Hydroxypropylmethylcellulose (5 cp) | 8.2 mg |
| Polyethylene oxide ** | 122.2 mg |
| Magnesium stearate | 0.4 mg |
| | 318.8 mg |

Exemplary formulation 2.1
Tablet composition in mg/tablet
(declared content = 30 mg of nifedipine
plus 50 mg of losartan potassium/tablet)

Osmosis layer

| | |
|---|---:|
| Hydroxypropylmethylcellulose (5 cp) | 8.0 mg |
| Sodium chloride | 46.5 mg |
| Polyethylene oxide *** | 102.9 mg |
| Red iron oxide | 1.6 mg |
| Magnesium stearate | 0.4 mg |
| | 159.4 mg |

Shell (osmotic membrane)

| | |
|---|---:|
| Cellulose acetate | 32.3 mg |
| Polyethylene glycol 3.350 | 1.7 mg |
| | 34.0 mg |

* Losartan-K granules = ground Lorzaar ® protect tablet (MSD Sharp & Dohme, Haar) comprising 50 mg of losartan potassium
** Polyox WSR N-80 NF (Dow); viscosity of 5% strength aqueous solution (25° C.): 40-100 mPa · s
*** Polyox WSR Coagulant NF (Dow); viscosity of 1% strength aqueous solution (25° C.): 5000-8000 mPa · s Production:

The components of the active ingredient layer are mixed and granulated dry. Likewise, the components of the osmosis layer are mixed and granulated dry. The two granules are compressed in a bilayer tablet press to a bilayer tablet (diameter 10 mm). The tablets are coated with an acetone solution of cellulose acetate and polyethylene glycol and dried. An orifice with a diameter of 0.9 mm is then made on the active ingredient side of each tablet using a hand drill.

In Vitro Release of Exemplary Formulation 2.1

| | Time [h] | | | | |
|---|---|---|---|---|---|
| Release [%] | 2 | 4 | 8 | 12 | 24 |
| Nifedipine | 2 | 23 | 53 | 84 | 101 |
| Losartan-K | 2 | 19 | 48 | 77 | 96 |

(USP-paddle, 100 rpm, 900 ml of phosphate buffer pH 6.8 + 1.0% sodium lauryl sulfate, JP sinker)

Exemplary formulation 2.2
Tablet composition in mg/tablet
(declared content = 30 mg of nifedipine plus 20 mg of telmisartan/tablet)

Core
Active ingredient layer

| | |
|---|---:|
| Nifedipine, micronized | 33.0 mg |
| Telmisartan granules * | 120.0 mg |
| Hydroxypropylmethylcellulose (5 cp) | 8.2 mg |
| Polyethylene oxide ** | 122.2 mg |
| Magnesium stearate | 0.4 mg |
| | 283.8 mg |

Osmosis layer

| | |
|---|---:|
| Hydroxypropylmethylcellulose (5 cp) | 7.1 mg |
| Sodium chloride | 41.4 mg |
| Polyethylene oxide *** | 91.65 mg |
| Red iron oxide | 1.4 mg |
| Magnesium stearate | 0.35 mg |
| | 141.9 mg |

Shell (osmotic membrane)

| | |
|---|---:|
| Cellulose acetate | 32.3 mg |
| Polyethylene glycol 3.350 | 1.7 mg |
| | 34.0 mg |

* Telmisartan granules = ground Kinzalmono ® tablet (Bayer AG, Leverkusen) comprising 20 mg of telmisartan
** Polyox WSR N-80 NF (Dow); viscosity of 5% strength aqueous solution (25° C.): 40-100 mPa · s
*** Polyox WSR Coagulant NF (Dow); viscosity of 1% strength aqueous solution (25° C.): 5000-8000 mPa · s Production:

The components of the active ingredient layer are mixed and granulated dry. Likewise, the components of the osmosis layer are mixed and granulated dry. The two granules are compressed in a bilayer tablet press to a bilayer tablet (diameter 10 mm). The tablets are coated with an acetone solution of cellulose acetate and polyethylene glycol and dried. An orifice with a diameter of 0.9 mm is then made on the active ingredient side of each tablet using a hand drill.

In Vitro Release of Exemplary Formulation 2.1

| | Time [h] | | | | |
|---|---|---|---|---|---|
| Release [%] | 2 | 5 | 10 | 15 | 24 |
| Nifedipine | 0 | 14 | 52 | 87 | 98 |
| Telmisartan | 5 | 22 | 51 | 80 | 90 |

(USP-paddle, 100 rpm, 900 ml of phosphate buffer pH 6.8 + 1.0% sodium lauryl sulfate, JP sinker)

The invention claimed is:

1. A pharmaceutical dosage form on the basis of an osmotic active ingredient release system, comprising a core and a semipermeable membrane which surrounds the core, wherein the core comprises an active ingredient combination of nifedipine or nisoldipine and at least one angiotensin II antagonist, wherein the semipermeable membrane is water-permeable but substantially impermeable to components of the core, and the semipermeable membrate includes at least one orifice, and wherein the release rates of the active ingredients differ from one another by no more than 25% absolute in the linear part of a release profile in a USB release method with apparatus 2 (paddle).

2. The pharmaceutical dosage form as claimed in claim 1, where the angiotensin II antagonist is selected from the group of candesartan, losartan, telmisartan, irbesartan and olmesartan or one of the prodrugs of these angiotensin II antagonists.

3. The pharmaceutical dosage form as claimed in claim 1, characterized in that 80% of the active ingredient combination are released in a period of from 8 to 24 hours in the USP release method with apparatus 2 (paddle).

4. The pharmaceutical dosage form as claimed in claim 3, characterized in that the release rates of the active ingredients differ from one another by not more than 15% absolute in the linear part of the release profile.

5. The pharmaceutical dosage form as claimed in claim 1, characterized in that the pharmaceutical dosage form is constructed so as to be solid and capable of oral administration, and on the basis of an osmotic active ingredient release system.

6. The pharmaceutical dosage form as claimed in claim 1, characterized in that the active ingredients are present in crystalline or predominantly crystalline form.

7. The pharmaceutical dosage form as claimed in claim 1, characterized in that the active ingredients are present in micronized form.

8. The pharmaceutical dosage form as claimed in claim 1, characterized in that the active ingredients are present wholly or partly in amorphous form.

9. The pharmaceutical dosage form as claimed in claim 1, characterized in that nifedipine or nisoldipine is employed in a minimum dose of 5 mg and a maximum dose of 60 mg.

10. The pharmaceutical dosage form as claimed in claim 1, characterized in that nifedipine or nisoldipine is employed in a minimum dose of 10 mg and a maximum dose of 40 mg.

11. The pharmaceutical dosage form as claimed in claim 1, characterized in that angiotensin II antagonist is candesartan, olmesartan, irbesartan, losartan or telmisartan.

12. The pharmaceutical dosage form as claimed in claim 1, characterized in that candesartan or one of its prodrugs is employed in a dose of 2-32 mg as angiotensin II antagonist.

13. The pharmaceutical dosage form as claimed in claim 1, characterized in that candesartan or one of its prodrugs is employed in a dose of 4-16 mg as angiotensin II antagonist.

14. The pharmaceutical dosage form as claimed in claim 1, characterized in that the angiotensin II antagonist olmesartan or one of its prodrugs is employed in a dose of 5-40 mg.

15. The pharmaceutical dosage form as claimed in claim 1, characterized in that olmesartan or one of its prodrugs is employed in a dose of from 10 to 40 mg.

16. The pharmaceutical dosage form as claimed in claim 1, characterized in that the angiotensin II antagonist is telmisartan and is employed in a dose of from 10 to 80 mg.

17. The pharmaceutical dosage form as claimed in claim 1, characterized in that telmisartan is employed in a dose of from 10 to 40 mg.

18. The pharmaceutical dosage form as claimed in claim 1, characterized in that losartan is employed in a dose of from 25 to 100 mg.

19. The pharmaceutical dosage form as claimed in claim 1, characterized in that losartan is employed in a dose of from 40 to 60 mg.

20. The pharmaceutical dosage form as claimed in claim 1, characterized in that irbesartan is employed in a dose of from 50 to 500 mg.

21. The pharmaceutical dosage form as claimed in claim 1, characterized in that irbesartan is employed in a dose of from 75 to 300 mg.

22. The pharmaceutical dosage form as claimed in claim 1 wherein the pharmaceutical dosage form is a single-chamber system.

23. The pharmaceutical dosage form as claimed in claim 1, wherein the core further comprises sodium chloride.

24. The pharmaceutical dosage form as claimed in claim 1, wherein the semipermeable membrane comprises cellulose acetate or a mixture of cellulose acetate and polyethylene glycol.

25. The pharmaceutical dosage form as claimed in claim 1, wherein the dosage form is a two-chamber system.

26. The pharmaceutical dosage form as claimed in claim 25,
wherein the core consists of an active ingredient layer comprising
5 to 50% of the active ingredient combination, and
40 to 95% of one or more osmotically active polymers,
and an osmosis layer comprising
40 to 90% of one or more osmotically active polymers, and
5 to 40% of an osmotically active additive.

27. The pharmaceutical dosage form as claimed in claim 26, which comprises in the active ingredient layer in the core polyethylene oxide with a viscosity of from 40 to 100 mPa·s (5% strength aqueous solution, 25° C.) as osmotically active polymer, and comprises in the osmosis layer in the core polyethylene oxide with a viscosity of 5000 to 8000 mPa·s (1% strength aqueous solution, 25° C.) as osmotically active polymer.

28. The pharmaceutical dosage form as claimed in claim 26, characterized in that the shell consists of cellulose acetate or a mixture of cellulose acetate and polyethylene glycol.

29. A process for producing an osmotic single-chamber system as defined in claim 22, characterized in that the components of the core are mixed together, granulated and tabletted, the core produced in this way is coated with a shell, and the shell is finally provided with one or more orifices.

30. A process for producing an osmotic two-chamber system as defined in claim 26, characterized in that
the components of the active ingredient layer are mixed and granulated, and
the components of the osmosis layer are mixed and granulated,
the two granules are then compressed in a bilayer tablet press to a bilayer tablet,
the core produced in this way is then coated with the semipermeable membrane, and
the semipermeable membrane is provided with one or more orifices on the active ingredient side.

31. A pharmaceutical comprising a pharmaceutical dosage form as claimed in claim 1.

32. The pharmaceutical dosage form as claimed in claim 1, in which the active ingredient combination further comprises an antihypertensive active ingredient.

33. The pharmaceutical dosage form as claimed in claim 1, in which the active ingredient combination further comprises a diuretic.

34. The pharmaceutical dosage form as claimed in claim 32, where hydrochlorothiazide is employed.

35. A method for the prophylaxis, secondary prophylaxis and/or treatment of cardiovascular disorders by administering a solid pharmaceutical dosage form of claim 1 which can be administered orally.

36. The method of claim 35 wherein the cardiovascular disorder is high blood pressure.

37. The pharmaceutical dosage form as claimed in claim 33, where hydrochlorothiazide is employed.

38. The pharmaceutical dosage form as claimed in claim 22, wherein the core comprises:
5 to 50% of the active ingredient combination,
10 to 50% xanthan, and
5 to 40% of a vinylpyrrolidone-vinyl acetate copolymer.

* * * * *